United States Patent [19]

Liu et al.

[11] Patent Number: 5,928,868
[45] Date of Patent: Jul. 27, 1999

[54] THREE HYBRID SCREENING ASSAY

[75] Inventors: Jun Liu, Cambridge, Mass.; Edward J. Licitra, Somerset, N.J.

[73] Assignee: Massachusetts Institute of Technology, Cambridge, Mass.

[21] Appl. No.: 08/845,674

[22] Filed: Apr. 25, 1997

Related U.S. Application Data

[60] Provisional application No. 60/017,341, Apr. 26, 1996.

[51] Int. Cl.$^6$ ............................. C12Q 1/68; C07H 21/04; C12N 15/00
[52] U.S. Cl. ............................. 435/6; 435/7.1; 435/29; 435/69.1; 435/69.4; 435/69.7; 435/70.1; 435/71.1; 435/465; 435/476; 435/483; 435/489
[58] Field of Search ............................. 435/6, 69.1, 69.4, 435/69.7, 70.1, 71.1, 7.1, 29, 465, 476, 483, 489

[56] References Cited

U.S. PATENT DOCUMENTS

| | | | |
|---|---|---|---|
| 5,283,173 | 2/1994 | Fields et al. | 435/6 |
| 5,362,629 | 11/1994 | Schreiber et al. | 435/21 |
| 5,468,614 | 11/1995 | Fields et al. | 435/6 |
| 5,498,597 | 3/1996 | Burakoff et al. | 514/2 |
| 5,610,015 | 3/1997 | Wickens et al. | 435/6 |
| 5,677,131 | 10/1997 | Wickens et al. | 435/6 |

FOREIGN PATENT DOCUMENTS

| | | |
|---|---|---|
| 91/04321 | 4/1991 | WIPO . |
| 91/13088 | 9/1991 | WIPO . |
| 93/03364 | 2/1993 | WIPO . |
| 94/18317 | 8/1994 | WIPO . |
| 94/23025 | 10/1994 | WIPO . |
| 95/02684 | 1/1995 | WIPO . |
| 95/24419 | 9/1995 | WIPO . |
| 95/30012 | 11/1995 | WIPO . |
| 95/34646 | 12/1995 | WIPO . |
| 96/02561 | 2/1996 | WIPO . |
| 96/06097 | 2/1996 | WIPO . |
| 96/06111 | 2/1996 | WIPO . |
| 96/13613 | 5/1996 | WIPO . |
| 96/29429 | 9/1996 | WIPO . |

OTHER PUBLICATIONS

Osborne, Mark A., et al., "The Yeast Tribrid System—Genetic Detection of trans–phosphorylated ITAM–SH2–Interactions" *Biotechnology*, (1995); vol. 13, p. 1474.

Gyuris, Jeno, et al., "Cdi1, a Human G1 and S Phase Protein Phosphatase That Associates with Cdk2." *Cell*, (1993); vol. 75, pp. 791–803.

Yang, Meijia, et al., "Protein–peptide interactions analyzed with the yeast two–hybrid system." *Nucleic Acids Research*, (1995); vol. 23, No. 7, pp. 1152–1156.

Durfee, Tim, et al., "The retinoblastoma protein associates with the protein phosphatase type 1 catalytic subunit." *Genes & Development*, (1993); vol. 7, No. 4, pp. 529–722.

(List continued on next page.)

*Primary Examiner*—Kenneth R. Horlick
*Attorney, Agent, or Firm*—Bromberg & Sunstein LLP

[57] ABSTRACT

Methods and a kit are provided for characterizing small molecules from a library of small molecules or alternatively identifying protein targets to which known small molecules bind. The methods include forming hybrid ligand in which at least one ligand is a small molecule. The hybrid ligand is introduced into cells that in turn contain a first and a second expression vector. Each expression vector includes DNA for expressing a hybrid protein that encodes a target protein linked to a coding sequence for a transcriptional module. The cells further contains a reporter gene, the expression of which is conditioned on the proximity of the first and second hybrid proteins to each other, an event that occurs only if the hybrid ligand binds to target sites on both hybrid proteins. Those cell which express the reporter gene are selected and the unknown small molecule or the unknown hybrid protein is identified.

33 Claims, 11 Drawing Sheets

OTHER PUBLICATIONS

SenGupta, Dhruba J., et al., "A three-hybrid system to detect RNA-protein interactions in vivo." *Proc. Natl. Acad. Sci. USA 93*, (1996); vol. 93, pp. 8496–8501.

Licitra, Edward J., et al., "A three-hybrid system for detecting small ligand-protein receptor interactions." *Proc. Natl. Acad. Sci, USA 93*, (1996); vol. 93, pp. 12817–12821.

Zhang, Jie, et al., "A Yeast Three-Hybrid Method to Clone Ternary Protein Complex Components." *Analytical Biochemistry*, (1996); Article No. 0429, pp. 68–72.

Belshaw, Peter J., et al, "Controlling Protein Association and Subcelluar Localization with a Synthetic Ligand that Induces Heterodimerization of Proteins", *Proc. National Acad. Sci. USA*, (1996), vol. 93, pp. 4604–4607.

Holsinger, Leslie J., et al, "Signal Transduction in T Lymphocytes Using a Conditional Allele of Sos", *Proc. Natl. Acad. Sci. USA*, (1995), vol. 92, pp. 9810–9814.

Pruschy, Martin N., et al, "Mechanistic Studies of a Signaling Pathway Activated by the Organic Dimerizer FK1012", *Chemistry & Biology*, (1994), vol. 1, No. 3, pp. 163–172.

Spencer, David J., et al, "Controlling Signal Transduction with Synthetic Ligands", (1993), *Science*, vol. 262, pp. 1019–1024.

Spencer, David J., et al, "A General Strategy for Producing Conditional Alleles of Src-like Tyrosine Kinases", *Proc. Natl. Acad. Sci. USA*, (1995), vol. 92, pp. 9805–9809.

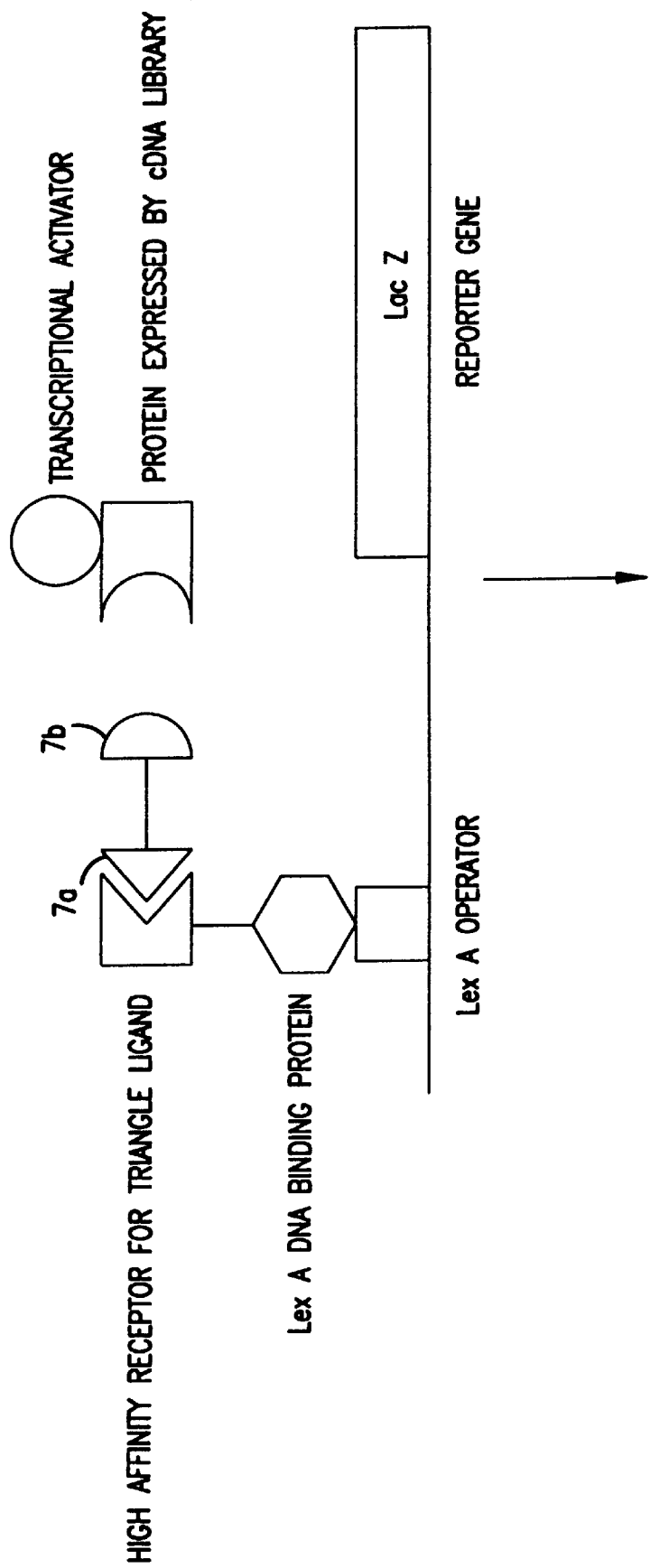

THREE HYBRID SCREENING ASSAY

The present application claims priority from U.S. provisional application No. 60/017,341, filed on Apr. 26, 1996 herein incorporated by reference.

TECHNICAL FIELD

The present invention relates to a generalized screening method and kit for small molecules that bind selected cellular targets and for targets capable of binding selected small molecules.

BACKGROUND OF THE INVENTION

A fundamental area of inquiry in pharmacology and medicine is the determination of ligand-receptor interactions. The pharmacological basis of drug action, at the cellular level, is quite often the consequence of non-covalent interactions between therapeutically relevant small organic molecules and high affinity binding proteins within a specific cell type. These small organic ligands may function as agonists or antagonists of key regulatory events which orchestrate both normal and abnormal cellular functions. For years the pharmaceutical industry's approach to discovering such ligands has been one of the random screening of thousands of small molecules in specific in vitro and in vivo assays to determine a potent lead compound for their drug discovery efforts. This lead compound often exerts very well-defined effects with regard to cell function (e.g. inhibition of cytokine production or DNA replication) but its mechanism of action at the molecular (ligand-protein interaction) level remains elusive. There is an unmet need for a general and efficient method to identify the cellular targets for these pharmacological agents so as to accelerate the search for novel drugs both at the basic and applied levels of research.

At this time, no efficient methodologies exist for rapidly identifying a biological target such as a protein for a particular small molecule ligand. Existing approaches include the use of affinity chromatography, radio-labeled ligand binding and photoaffinity labeling in combination with protein purification methods to detect and isolate putative target proteins. This is followed by cloning of the gene encoding the target protein based on the peptide sequence of the isolated target. These approaches depend on the abundance of the putative target protein in the sample and are laborious and painstaking. There is no existing technology allowing for the direct identification of the cDNA encoding a target for a given ligand.

Similarly, no efficient general approach exists for identifying a small molecule capable of binding any selected cell target regardless of its biological function. Fowlkes et al. and Broach et al (WO 94/23025, WO 95/30012) developed a screening assay for identifying molecules capable of binding cell surface receptors so as to activate a selected signal transduction pathway. These references describe the modification of selected yeast signaling pathways so as to mimic steps in the mammalian signaling pathway. This latter approach is specific for certain signaling pathways and has limited utility for broadly discovering small molecules that interact with any cellular target.

Recently, a yeast genetic screening method has been developed for specifically identifying protein-protein interactions in an in vivo system. This assay is known as the Yeast Two-Hybrid system. (see FIG. 1, U.S. Pat. No. 5,468,614; and Yang et al. (1995) Nucleic Acid Research 23, 1152–1156). The yeast Two-Hybrid system relies on the interaction of two fusion proteins to bring about the transcriptional activation of a reporter gene such as E.coli derived β-galactosidase (Lac Z). One fusion protein comprises a preselected protein fused to the DNA binding domain of a known transcription factor. The second fusion protein comprises a polypeptide from a cDNA library fused to a transcriptional activation domain. In order for the reporter gene to be activated, the polypeptide from the cDNA library must bind directly to the preselected target protein. Yeast cells harboring an activated reporter gene can be differentiated from other cells and the cDNA encoding for the interacting polypeptides can be easily isolated and sequenced. However, this assay is unsuited for screening small molecule-protein interactions because it relies solely on genetically encoded fusion proteins.

There is an unmet need for a general screening method to determine the interaction between small molecules and protein targets so as to identify new drugs that are capable of specific therapeutic effects in a variety of disease states as well as to identify agonists and antagonists that may interfere or compete with the binding of the small molecules for these targets.

SUMMARY OF THE INVENTION

The invention disclosed herein provides a rapid method and kit for identifying the targets of biologically active small molecules so as to identify new drugs that are capable of specific therapeutic effects as well as to identify novel small molecules including agonists and antagonists that may bind selected targets.

The invention is directed to a method for providing a genetic system capable of detecting pharmacologically relevant small ligand-protein interactions. Furthermore, the invention may be used to screen a multitude of proteins for interactions with any small ligand. The intention of this method is to identify the biologically relevant receptor for a pharmacological agent. A further use of the invention is to provide a method for high throughput pharmacological screens in both yeast and mammalian cells to identify novel ligand which binds to a known cellular target.

In a preferred embodiment, a method is provided for identifying a cellular component to which a small molecule is capable of binding, the method having the following steps; providing a hybrid molecule consisting essentially of two ligands, identified as ligand A and ligand B, that are covalently linked, wherein ligand A has a specificity for a predetermined target; and ligand B is the small molecule; introducing the hybrid molecule into at least one sample, the sample containing an environment, the environment containing a first expression vector, including DNA encoding the target for ligand A linked to a coding sequence for a first transcriptional module for expression as a first hybrid protein; a second expression vector including a random DNA fragment encoding a polypeptide fused to a second transcriptional module for expression as a second hybrid protein; and a third vector including a reporter gene wherein the expression of the reporter gene is conditioned on the proximity of the first and second hybrid proteins. The hybrid molecule is permitted to bind to the first hybrid protein through ligand A and to the second hybrid protein through ligand B so as to activate the expression of the reporter gene. Those samples expressing the reporter gene are identified and the second hybrid protein is characterized in the identified samples so as to determine the cellular component to which the small molecule is capable of binding.

In a preferred embodiment, a method is provided for identifying a small molecule capable of binding a molecular target, comprising the steps of; (a) providing a preparation of a library of hybrid molecules wherein each hybrid consists essentially of two ligands identified as ligand A and ligand B, that are covalently linked, wherein ligand A has a specificity for a first predetermined target and ligand B is a random small molecule; and (b) introducing the preparation into at least one sample, the samples containing an environment, wherein the environment contains; a first expression vector, including DNA encoding the target for ligand A, linked to a coding sequence for a first transcriptional module for expression as a first hybrid protein; a second expression vector including DNA encoding a second predetermined target for identifying a putative interacting ligand, linked to a coding sequence for a second transcriptional module for expression as a second hybrid protein; and a third vector including a reporter gene wherein the expression of the reporter gene is conditioned on the proximity of the first and second hybrid protein. The hybrid molecules are permitted to bind to the first hybrid protein and the second hybrid protein so as to activate the expression of the reporter gene. Those samples expressing the reporter gene are identified and ligand B, corresponding to the interacting ligand, is characterized so as to determine the small molecule capable of binding to the molecular target.

In a preferred embodiment, a method is provided for identifying a small molecule capable of competitively binding a molecular target, in the presence of a known binding ligand, the method having the following steps; (a) providing hybrid molecules consisting essentially of two ligands, identified as ligand A and ligand B, that are covalently linked, wherein ligand A has a specificity for a first predetermined target and ligand B has a specificity for a second predetermined target; (b) introducing the hybrid molecules into at least one sample, the samples containing an environment, wherein the environment contains; a first expression vector, including a DNA encoding the first predetermined target, linked to a coding sequence for a first transcriptional module for expression as a first hybrid protein; a second expression vector including DNA encoding the second target, linked to a coding sequence for a second transcriptional module for expression as a second hybrid protein; a third vector including a reporter gene wherein the expression of the reporter gene is conditioned on the proximity of the first and second target; and at least one random small molecule identified as ligand C. The hybrid ligand molecules are permitted to bind the first and second target to activate the reporter gene in the presence of ligand C. The samples are identified according to the absence of expression of the reporter gene; and ligand C is characterized so as to determine the identity of the small molecule binding competitively to the molecular target.

In a preferred embodiment, a kit is provided for detecting interactions between pharmacologically relevant small molecules and proteins, having the following elements; (i) a preactivated ligand A and reagents for forming a hybrid molecule with at least one type of a ligand B; (ii) a first expression vector including DNA encoding the binding protein for Ligand A linked to a coding sequence for a first transcriptional module for expression as a first hybrid protein; (iii) a second expression vector including a random DNA fragment encoding a polypeptide linked to a coding sequence for a second transcriptional module for expression as a second hybrid protein; (iv) a third vector including a reporter gene wherein transcription of the reporter gene is conditioned on the proximity of the first and second target proteins; (v) an environment for transcription and translation of the hybrid proteins and reporter genes; and (vi) a means for detecting the expression of the reporter gene following the formation of a trimeric complex between the hybrid ligand and the hybrid proteins.

DETAILED DESCRIPTION OF SPECIFIC EMBODIMENTS

According to the invention, "a screening assay" is defined here and in the claims as a process for selecting or eliminating items by means of at least one distinctive criteria. The screening assay is intended to be distinct from any assay of biological function or effect. The items in this method are small molecules, and the selection is based on capability of binding a target molecule (sometimes called a receptor). A feature of the screening assay is the ability to rapidly examine the binding of large numbers of different small molecules for selected target molecule and conversely, to examine the binding of selected molecules for a large number of target molecules. The positive interaction between small molecules and a target results in a chemical signal that is quantitatively and/or qualitatively different from a signal if any produced in the negative control.

"The sample containing an environment" is defined here and in the claims as a sample containing a complex biochemical mixture such as is found within a eukaryotic or prokaryotic cell or alternatively may be formed from a cell lysate maintained in a synthetic boundary such as a membrane or a reaction vessel.

"A cell component" is defined here and in the claims as including any of a nucleic acid, a polysaccharide, a lipid, or a protein or any combination of these.

A "reporter gene" is defined here and in the claims as a marker for detecting the formation of a three hybrid complex. The reporter is not intended in itself to have a therapeutic effect in the environment within which it is located in the assay.

Figure 3A:
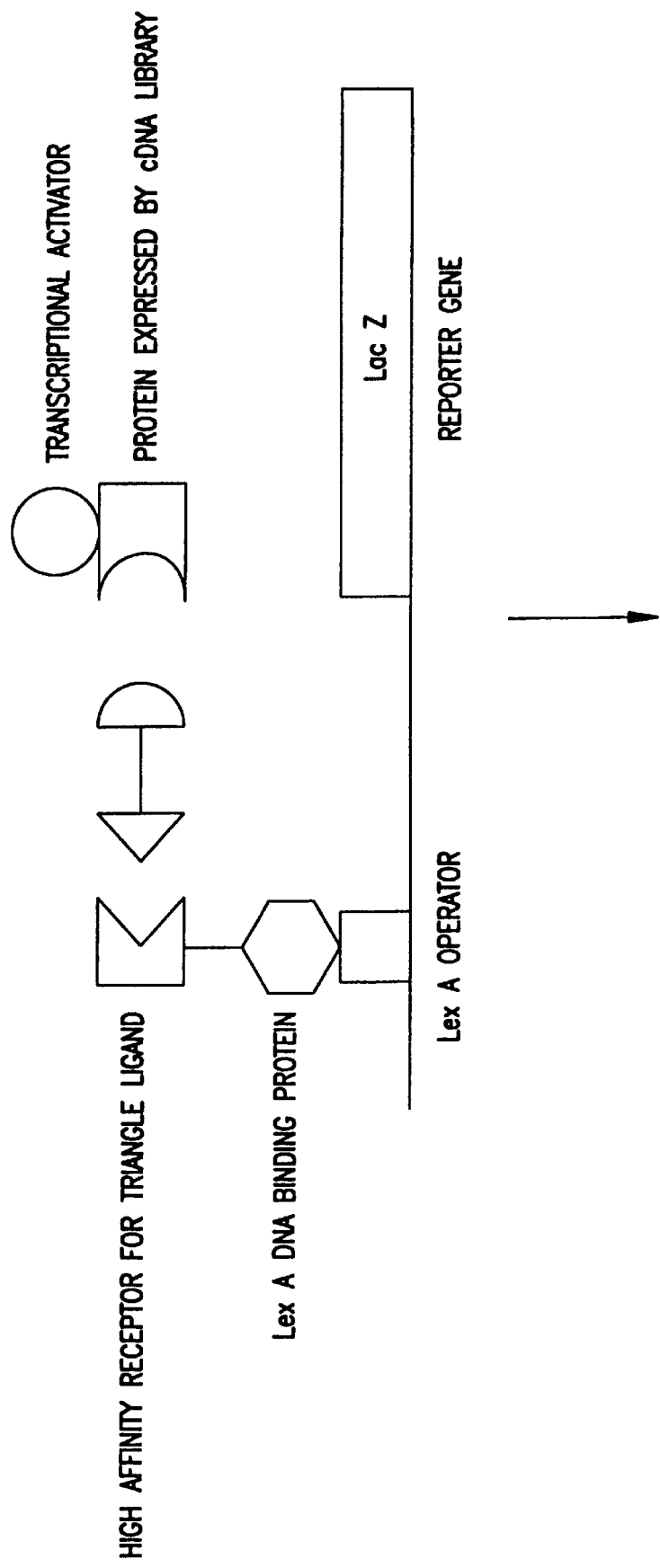
FIG. 3 is a diagrammatic representation of a generalized sequence of events during a three hybrid screen: (a) addition of the hybrid ligand (7) into an environment containing recombinant fusion vectors; (b) binding of the ligand (7a) to a high affinity receptor binding ligand (1); (c) binding of the small molecule ligand (7b) to a protein expressed by the cDNA (4)
Figure 3C:
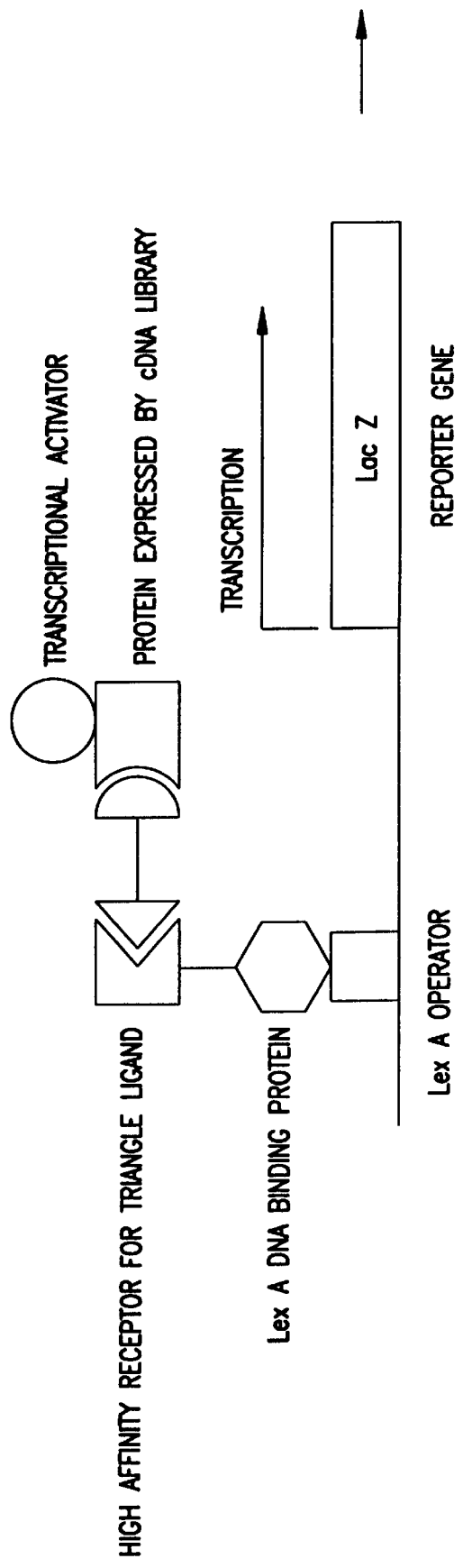

The novel three hybrid assay is described in FIG. 3. and involves the formation of a complex between a hybrid ligand, and two hybrid proteins in which one component of the three hybrid complex may be unknown. The unknown component in the assay may be either the small molecule contained in the hybrid ligand, or one of the hybrid proteins. There is no requirement that the unknown component be purified prior to the screening assay. Indeed, it is expected that the unknown component be contained in a mixture containing a large number of components, some or all being unidentified. These interactions may be determined in vivo or in vitro when the three hybrid complex triggers the expression of at least one reporter gene that can be detected by an appropriate assay.

Examples of the utility of the assay include: (1) determining the identity of target molecules having a binding affinity with a known small molecule where the small molecule has pharmacologic activity and where the target molecules may be suited for therapeutic intervention in a variety of disease states; (2) determining the identity of a small molecule capable of direct binding to a known target molecule where the identified small molecules may be suitable as therapeutic agents; (3) determining the identity of a small molecule capable of binding competitively to a known target molecule in the presence of a hybrid molecule so as to inhibit the binding between the target and the preselected small molecule; (4) developing a high throughput pharmacological assay in a number of cell types and organisms to screen for drug candidates; and (5) selecting novel small molecule for binding novel targets with high affinity using an iterative process of direct and competitive screening steps. For example a known small molecule may be used to identify a target and subsequently the target may be used to identify a novel small molecule. This approach can provide novel small molecule pharmacologic agents and may also provide highly specific reagents for use in screening for small molecules in the environment. The advantages of this assay are described in Licitra et al. PNAS 93, 12817–12821 herein incorporated by reference.

Figure 1:
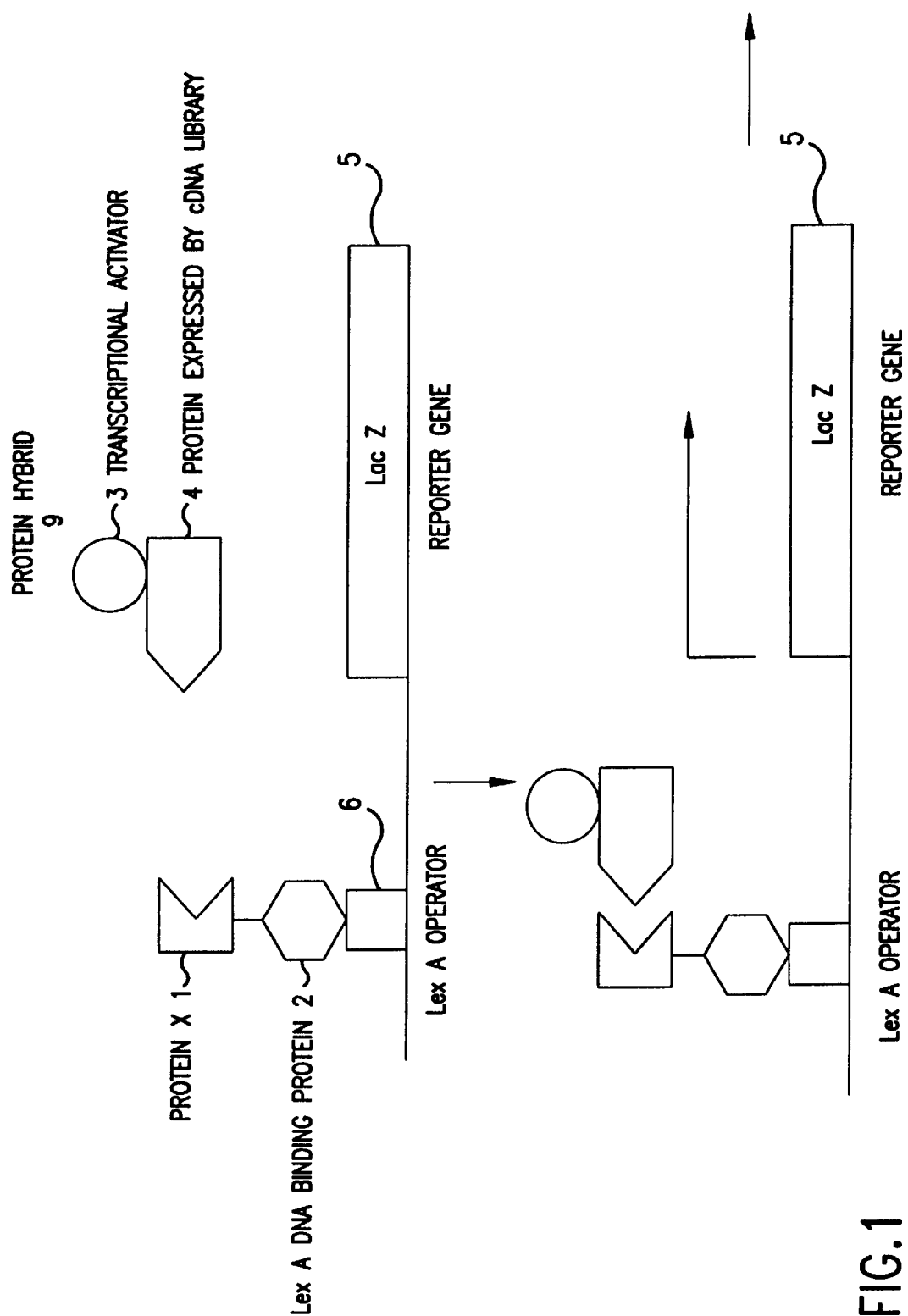
FIG. 1 is a diagrammatic representation of the yeast two hybrid assay showing the interaction between a protein X (1), Lex A DNA binding protein (2) and transcriptional activator (3), protein expressed by cDNA (4), which triggers the expression of the Lac Z reporter gene (5), subsequent to the interaction of the transcriptional activator modules with the Lex A operator (6).
Figure 2:
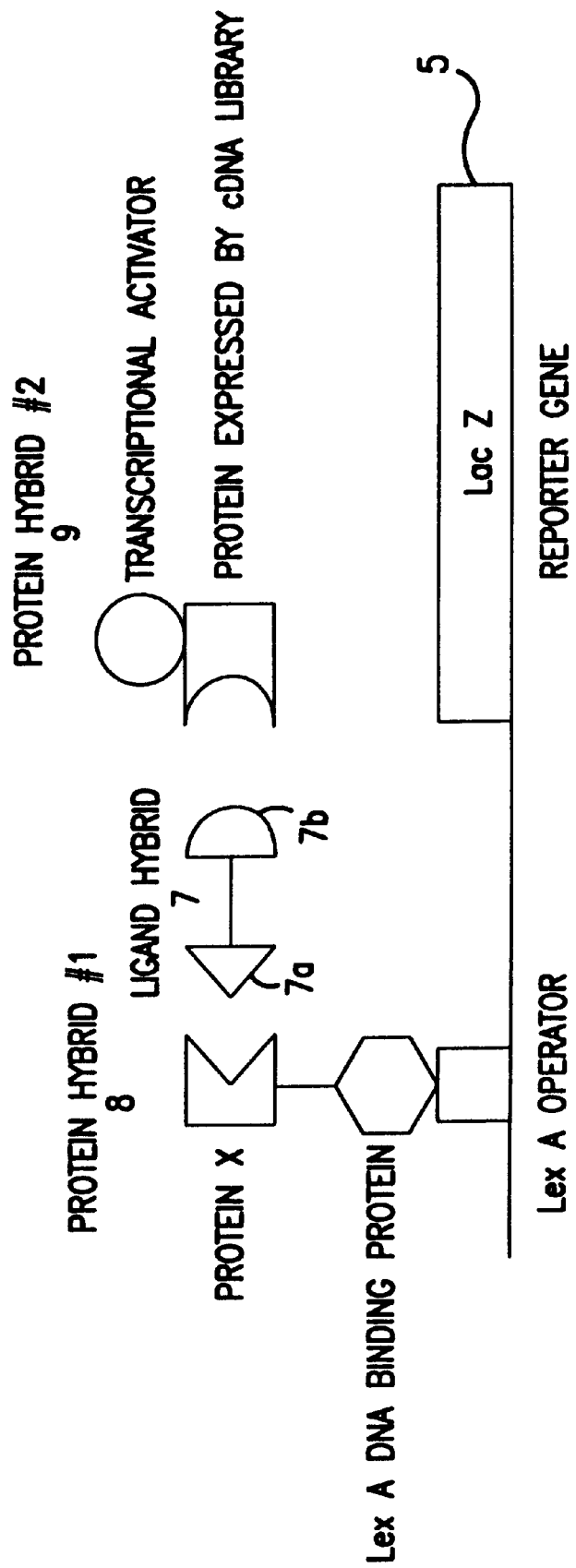
FIG. 2 is a diagrammatic representation of the components of the three hybrid assay showing a known target protein (8), Lex A DNA binding protein (2), transcriptional activator (3), protein expressed by cDNA (4), the Lac Z reporter gene (5), and the Lex A operator (6).

The method identified here as the three-hybrid system includes the step of providing a hybrid molecule, consisting of two covalently -linked small ligands identified as ligand A and ligand B, wherein ligand A has a specificity for a predetermined target and ligand B is the small molecule. (FIG. 2)

Figure 4:
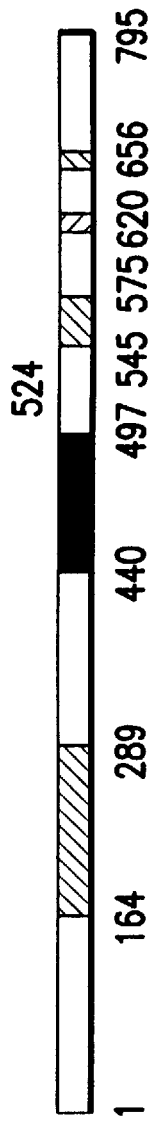
FIG. 4 provides a map of the protein domains of the rat glucocorticoid receptor.
Figure 5:
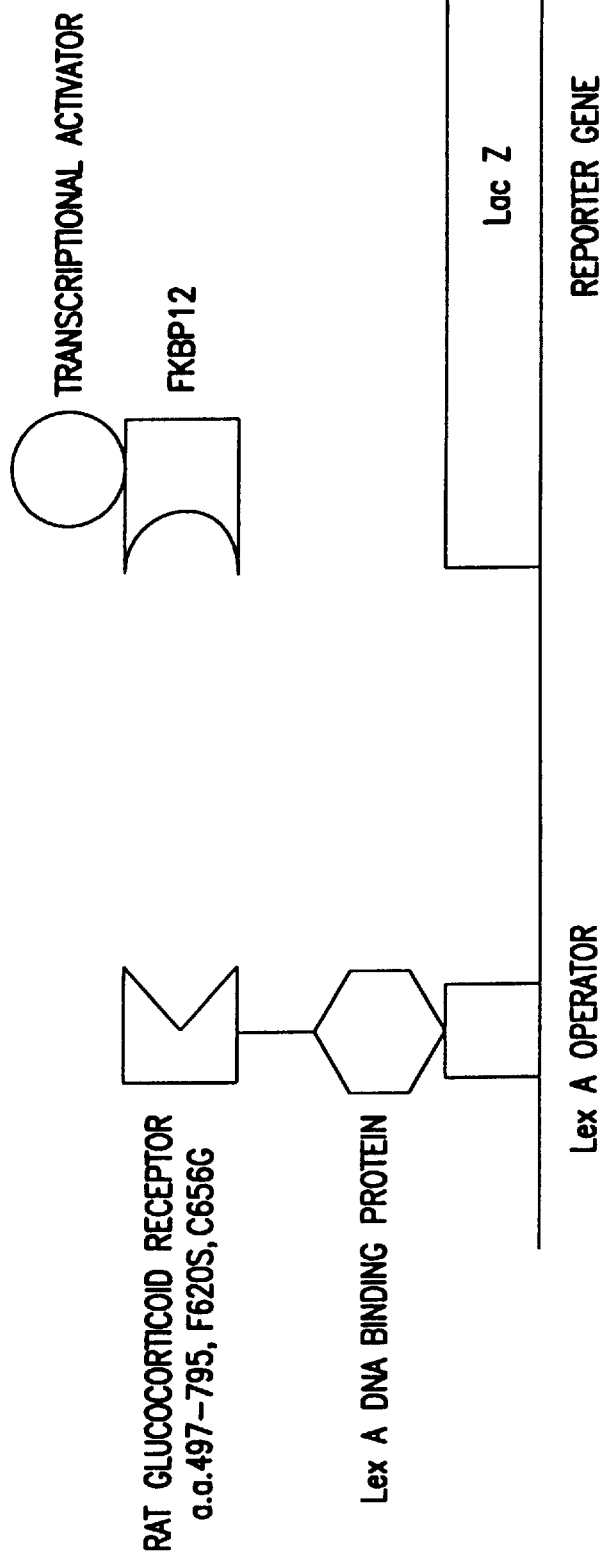
FIG. 5 is a diagrammatic representation of the proteins expressed in transformed yeast as used in Example 1 in the absence of a hybrid ligand, where one transcription factor is the Lex A DNA binding protein (2) which is fused to the hormone-binding domain of the rat glucocorticoid receptor protein aminoacid 497-795 F620S,C656G (8) and the second transcription factor is the transcriptional activator (3) fused to FKBP12 protein (4).
Figure 6:
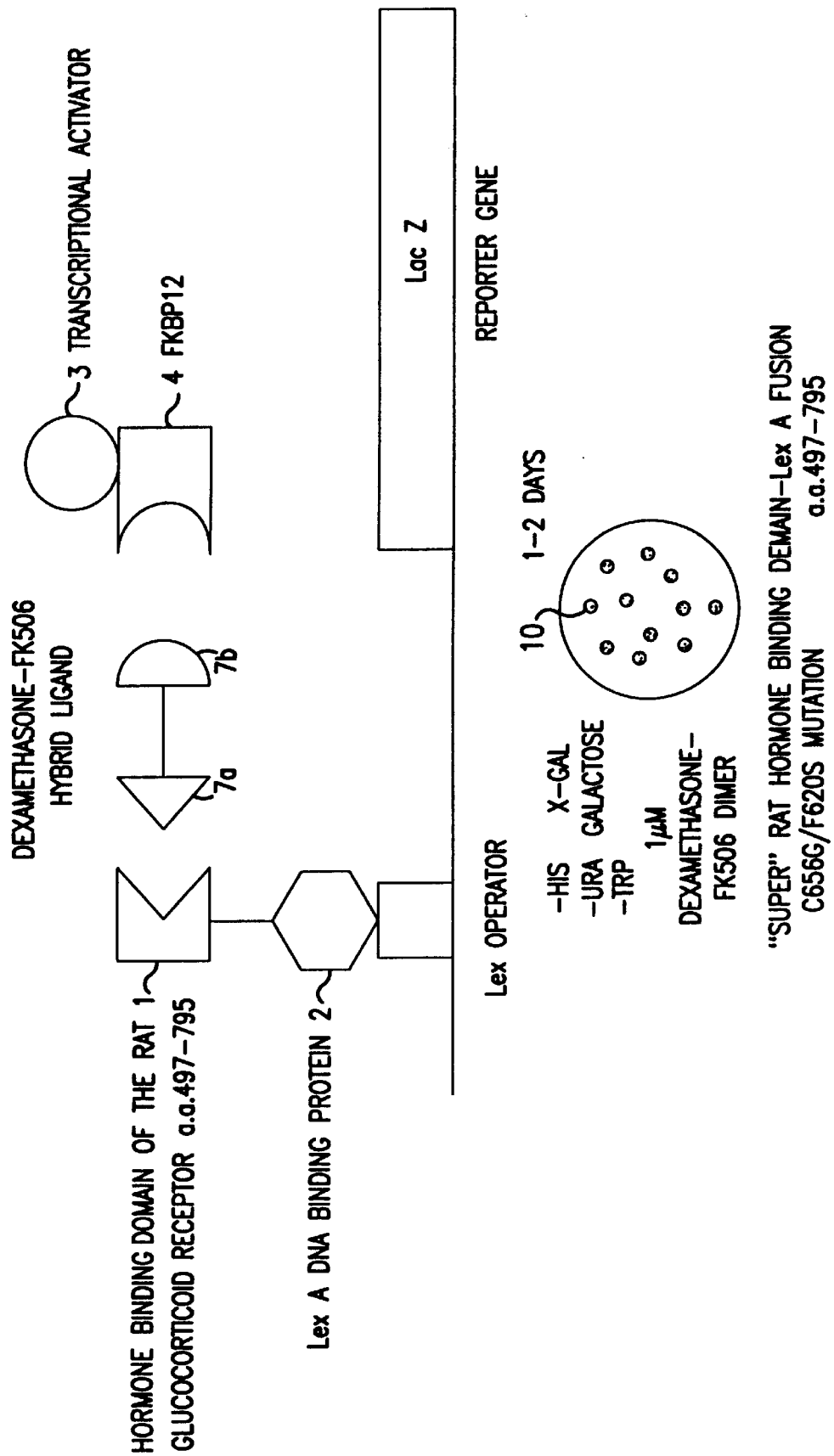
FIG. 6 illustrates a plate with His⁻Ura⁻Trp⁻XGal galactose (9) after 1–2 days, containing blue colonies (10) that are expressing β-galactosidase; adjacent to a diagram of the molecular events necessary for the expression of β-galactosidase to occur (as in FIG. 5) and including a hybrid ligand consisting of 1 $\mu$M dexamethasone (7a)-F506 dimer (7b).

The three hybrid assay was shown to be an effective assay using a test system. This test system is exemplified in Examples 1 and 4. FIGS. 4–6, utilizes as the small molecule (ligand A), the steroid molecule, dexamethasone, which binds the glucocorticoid receptor with high affinity. Dexamethasone is modular in nature; it can be covalently linked to another small molecule such as biotin without losing its affinity for the glucocorticoid receptor. The use of steroids such as dexamethasone is advantageous in that these molecules are highly membrane permeable and are small in size. The method of the invention may utilize other steroid molecules as well as small molecules other than steroids as ligand A. Other ligands such as cyclosporin (MW 1200) may also be used where the target or receptor to which the ligand is bound has been identified in the art. Furthermore, the small molecule may be identified in a hybrid ligand according to its ability to form a covalent bond with its target molecule. For example, β lactamase (target molecule) may covalently bind suicide inhibitors (ligand A) such as β-lactam antibiotics. (Example 3)

In contrast to ligand A, Ligand B can be a random molecule of unknown identity obtained from a combinatorial library, or other small molecule archive. Examples of combinatorial libraries include but are not limited to peptide libraries, nucleic acid libraries, polysaccharide libraries, and small organic molecules. Archives of molecules include collections of environmental molecules and molecules from chemical processes. According to the invention "small molecule" may be defined here and in the claims as having a molecular weight of less than 1000 D more particularly less than 800 D and greater than 50 D. The test system exemplified in example 1, utilizes as ligand A, FK506 protein (MW 850) which binds an FK binding protein (FKBP).

The covalent hybrid linkage between ligand A and ligand B may be formed by any of the methods known in the art. (for example: Jerry March, Advanced Organic Chemistry (1985) Pub. John Wiley & Sons Inc; and HH, House, Modern Synthetic Reactions (1972) pub. Benjamin Cummings) Example 1 and FIG. 7 describes an embodiment of a linkage reaction between dexamethasone and FK506. Descriptions of linkage chemistries are further provided by Crabtree et al. WO 94/18317, 95/02684, Schreiber et al WO 96/13613, Holt et al. WO96/06097; these references being incorporated herein by reference.

Figure 9:
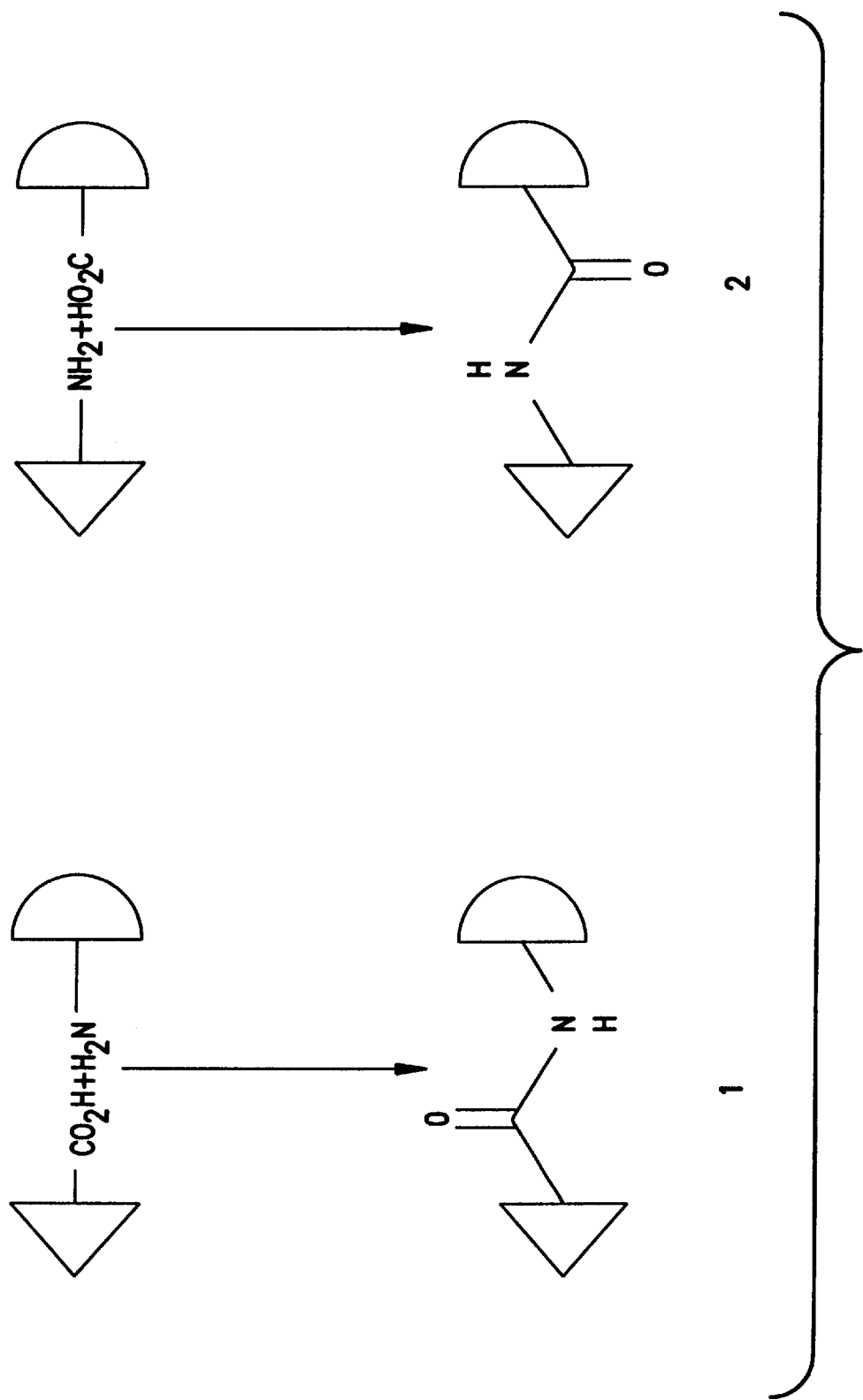
FIG. 9 is a diagrammatic illustration of an electrophilic ligand and a nucleophilic ligand capable of forming an amide linkage.

In an embodiment of the invention, a single ligand or small molecule having electrophilic properties such as a terminal carboxylic acid group may be linked to a ligand or small molecule having nucleophilic properties such as an amino group by means of condensation (FIG. 9). Small molecules may be coupled to reasonably large ligands (up to 5000 D) to form hybrid ligands without significantly losing membrane permeability.

According to the method of the invention, the hybrid ligand is introduced into a sample, the sample containing an environment as defined above. The environment is characterized by a functional transcription and translation apparatus. This environment may be whole cells, cell lysate or a synthetic mixture of enzymes and reagents. It is desirable that components of the assay including vectors and hybrid molecules be readily introduced into the environment. An example of an environment that is cellular, is eukaryotic cells, more particularly a yeast cell population, more particularly Saccharomyces cerevisiae or Schizosaccharomyces pombe; other examples include invertebrate cell lines such as Drosophila cells, and mammalian cells. Cells capable of use in a three hybrid assay include primary cultures, cultures of immortalized cells or genetically manipulated strains of cells. Different cell types may be selected for the three hybrid assay according to the permeability of the cells to selected hybrid ligands. Another criteria for selection of a particular cell type may be the nature of post translational modification of proteins expressed by the recombinant vectors where the binding of such modified proteins to a small molecule may more accurately mimic the natural state. The assay may be performed using single cells or populations of cells for each test sample.

According to the method of the invention, the introduction of the hybrid ligand into the environment, may include traversing a membrane so as to enter the cell. The hybrid molecule is introduced into cells by electroporation or any permeation procedures that is known in the art. In certain embodiments, cells may be used which may be genetically or pharmacologically modified to increase the intracellular concentrations of the hybrid ligand. These include procedures that utilize polybasic peptides such as polymixin B or genetically altered strains of cells which offer increased permeability or decrease efflux of hybrid ligand. A hybrid ligand may be selectively formed having an overall charge and polarity that facilitates transmembrane transport.

According to the three hybrid assay, the environment contains three different types of vector. Two of the vectors encode fusion or hybrid proteins, each hybrid protein including a transcription module and a target molecule for binding ligand A or ligand B of the hybrid ligand. Once the three hybrid complex is formed, and the transcription modules are brought into close proximity, the transcriptional activation of a reporter gene occurs. This is exemplified in Example 1.

Transcription factors bind to specific DNA sequences adjacent to the gene to be transcribed thereby facilitating the functioning of the transcriptional machinery. It is well established that many transcription factors possess two modular domains which are separable in function. (Mendelsohn and Brent (1994) Current Opinions in Biotechnology, incorporated by reference). In eukaryotic transcription systems, the DNA binding module is not physically on the same peptide as the transcription activation module. The first module is responsible for recognizing the sequence gene in the promoter region particular gene in the promoter region and the second is a more general module which consists of a number of acidic amino acid residues that act as transcriptional enhancers. Where the modules are encoded on separate vectors, an event is required that brings the transcription activating modules together so as to initiate transcription of the reporter gene.

Several transcriptional activation modules have been identified as described by Mendelsohn and Brent (1994), and by Crabtree et al (WO 95/02684). Any of these may be suited for use in the three-hybrid system. In particular, Example 1 utilizes the E.Coli Lex A DNA binding protein that binds tightly to Lex A operator and activates transcription of a reporter gene such as Lac Z. A wide variety of transcriptional activation domains can be used including the bacterial B42 transcriptional activator GAL 4, (Example 2), GCN4 and VP16. The DNA encoding transcriptional activator modules are incorporated into vectors that are capable of being expressed in eukaryotic cells. Adjacent to these sequences is inserted DNA encoding target protein (first expression vector) or unknown gene products (second expression vector) such that a fusion protein is expressed by the eukaryotic cell. Vectors containing transcription modules are described in the art and any of these may be used according to the assay. (Licitra et al. (1996)).

Figure 8:
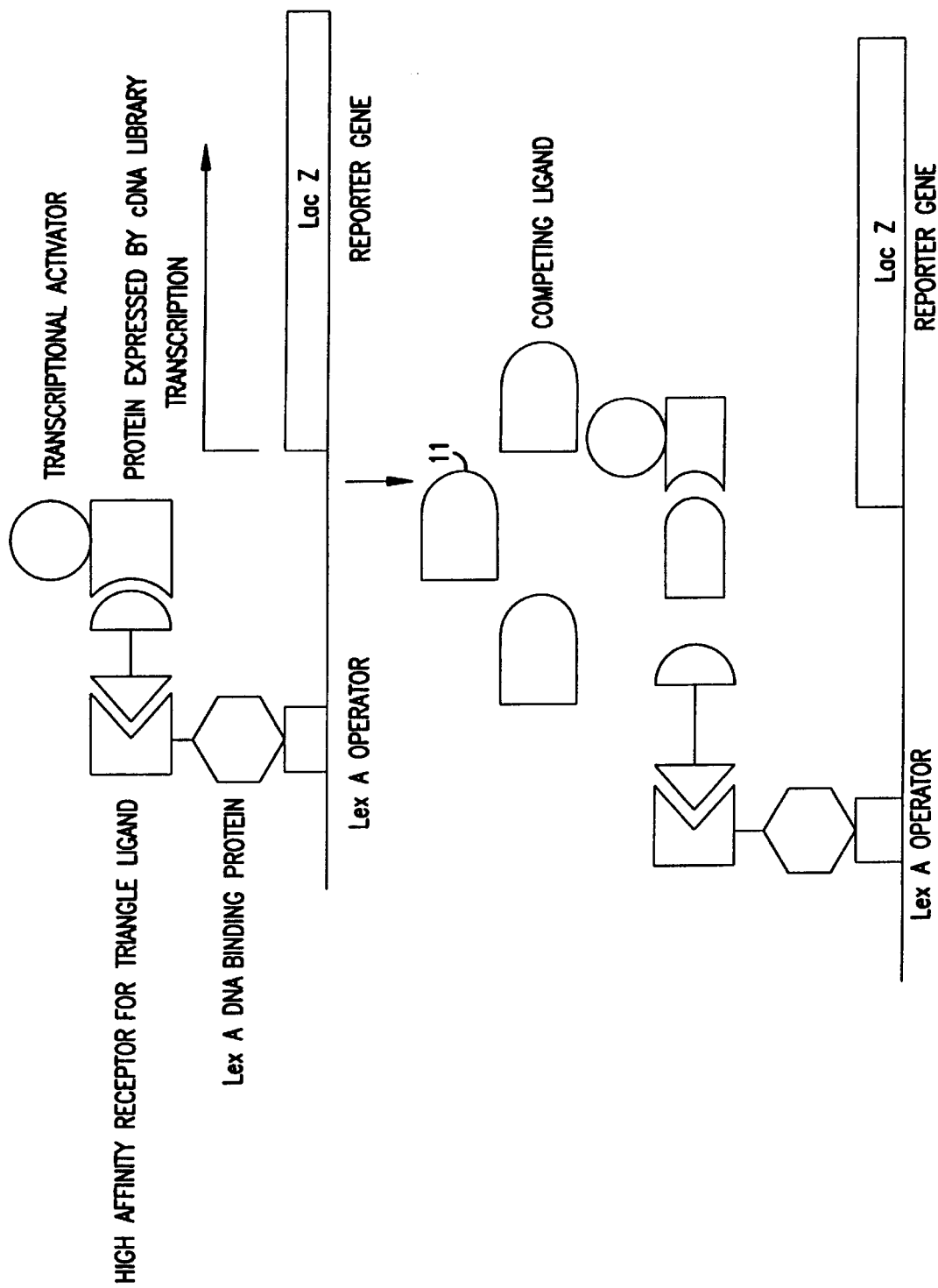
FIG. 8 illustrates the molecular events in a competitive assay where the antagonists (11) can be any small molecule.

An application of the three hybrid assay is when the small molecule has a known pharmacological function but unknown target, the unknown targets being established by means of the assay (Example 1). The target molecule may be any cellular component including a nucleic acid, a polysaccharide, a lipid or a protein or a combination of any of these. In the examples provided below, the target is a protein encoded by DNA. Cloned DNA encoding target protein may be inserted by standard cloning techniques. Alternatively, random DNA sequences of a size that is capable of encoding a yet undetermined target protein, may be inserted in the second expression vector where the random DNA sequences are derived from a genomic DNA library, cDNA library or synthetically generated library formed from eukaryotic cells, prokaryotic cells, viruses or formed by an automated DNA synthesizer. (Current Protocols in Molecular Biology, ch 9). Examples of target proteins encoded by a plasmid library may include enzymes, oncogene products, signaling proteins, transcription factors and soluble domains of membrane proteins. An alternative application of the three hybrid assay is when the nature of the target molecule is known and a small molecule is sought that is capable of binding the target molecule. This type of assay may be a direct assay (Examples 1, 2) or a competitive binding assay (Example 5, FIG. 8).

The third vector contained in the environment is a vector encoding a reporter protein which is switched on in the presence of united transcription activation modules. Reporter genes are so named because when transcribed and translated, they can be detected according to a phenotype based on a selectable characteristic such as growth in an appropriate growth media or visual screening. In a preferred embodiment of the invention, reporter genes that permit visual screening are utilized. Examples of reporter gene products that may be detected visually include β-galactosidase and *Aequorea victoria* Green Fluorescent Protein (GFP), antibodies or selected antigens. These gene products may be identified visually or by spectrophotometric quantification.

The switching on or off of the reporter gene depends in part on the binding affinity of the small molecule ligand to the target so as to activate the reporter gene or to competitively inhibit the activation of the reporter gene. The affinity of a ligand or small molecule for a target molecule may vary substantially in the three-hybrid screen. An example of a range of binding affinities includes a Kd having a value below $10^{-6}$, more preferably below $10^{-7}$ and even more preferably below $10^{-8}$ and in some embodiments below about $10^{-9}$. An example of a dissociation constant includes a range less than 10 $\mu$M. This does not preclude the effectiveness of a binding affinity outside this range. Ligand A may be selected on the basis of substantially defined structure activity data concerning binding to a known target; established chemistry for linking the ligand to a small molecule; and strong binding affinity for a target encoded by a fusion gene.

A feature of the three-hybrid system includes the formation of a hybrid ligand molecule. The consequence of the hybrid molecule binding to both target hybrid molecules is a three hybrid complex that results in the stimulation of transcription of at least one reporter gene. The detection of a positive result may follow from direct binding of a hybrid ligand to target hybrid molecules or by competitive binding of the hybrid ligand acting as an agonist or antagonist. In certain circumstances, the target molecule for therapeutic intervention may be known but a suitable small molecule for binding the target molecule may be desired. If no candidate small molecule for binding the target is known, it may be desirable to generate a random library of hybrid molecules in which a mixture of small molecules are chemically modified in such a way as to bind to a preselected ligand. Subsequently, pools of molecular hybrids may be introduced into an environment such as yeast cells for performing the three-hybrid system. Those sample that are positive can be reanalyzed using increasingly smaller subsets of the initial pool until a single candidate small molecule type is discovered.

Alternatively, a candidate small molecule that binds a selected target molecule may be known, but it is desirable to select a small molecule with improved binding affinity for the target molecule. In this situation, a molecular hybrid of the candidate small molecule and a ligand is formed and the three hybrid screening assay is performed in the presence of a library of small molecules that compete with the molecular hybrid for binding the target. Those samples which contain small molecules having improved binding to the target molecule, compared with the candidate small molecule, will not activate the reporter gene.

In one embodiment of the invention, a kit is provided containing a ligand with a suitably charged reactive group. The kit further includes reagents for attaching the ligand to a small molecule for utilization in a three-hybrid system. In another embodiment of the invention, a kit is provided for practicing the method of the invention. The kit may include a reaction chamber, at least two vectors, a host cell and a ligand with a suitably charged reactive group for reaction with a small molecule. The two vectors encode hybrid proteins as described below in Example 1.

EXAMPLE 1

Identification of the Cellular Component to which the Small Molecule FK506 Binds FK506 is a well studied small organic molecule which binds to a family of proteins known as FK506 binding proteins (FKBP) with binding affinities in the nanomolar range. There are a number of previously identified FKBPs including FKBP12, FKBP 13, FKBP 25 and FKBP59. The FK506 molecule, similar to many proteins, is modular in nature. FK506 possesses two separable regions, one responsible for binding of the FKBPs and the other responsible for conferring immunosuppressive activity and appropriately termed the effector domain. The FK506 molecule binds with low nanomolar binding affinity to many of the FKBPs when linked through the effector domain and serves as an effective small molecule for proving the efficacy of the three-hybrid system. Additionally, since the FKBPs possess binding affinities ranging from sub-nanomolar to several hundred nanomolar for FK506, this choice permits the assessment of the sensitivity of the method when screening a library.

Figure 7A:
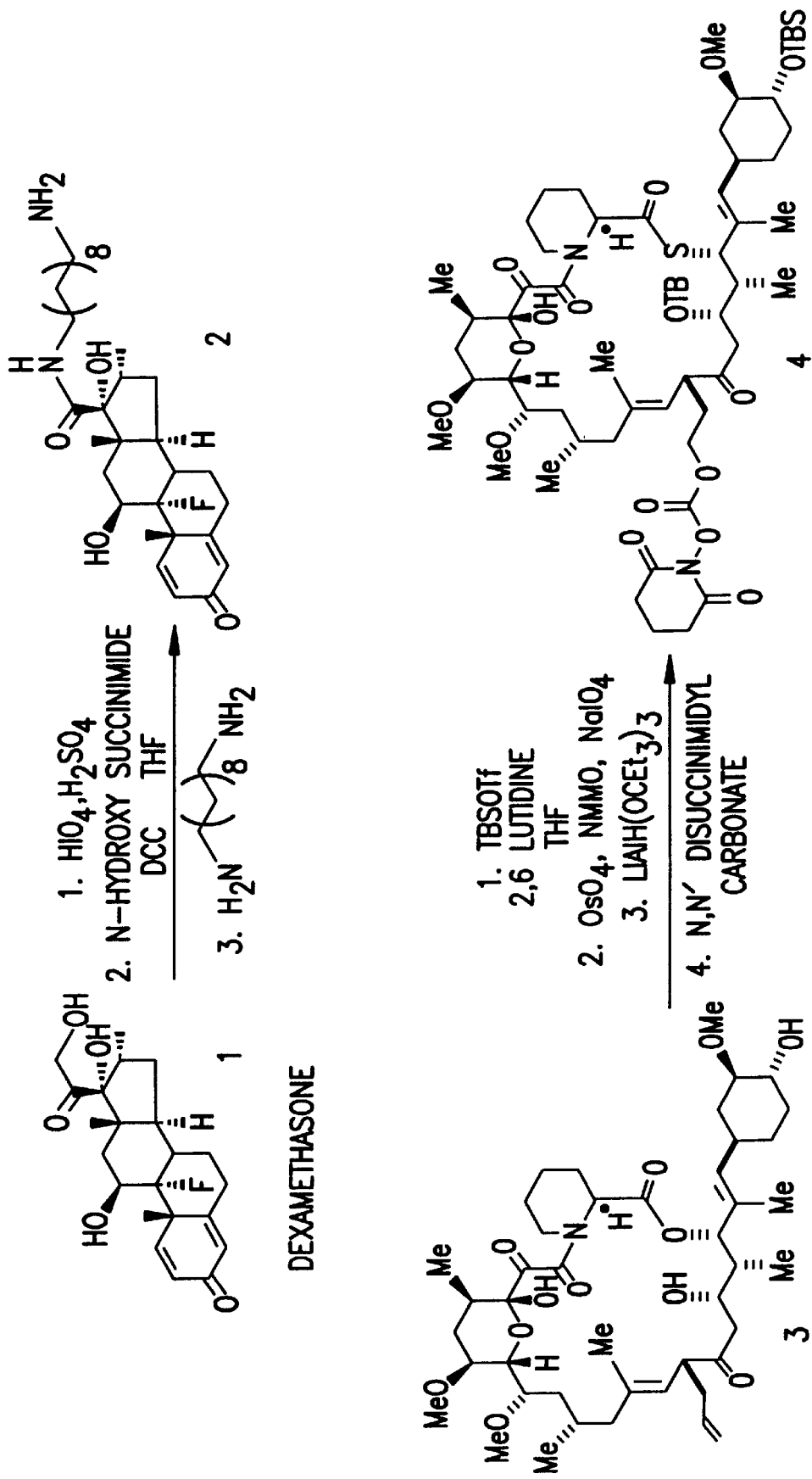
FIG. 7 illustrates the synthesis of the hybrid molecule.
Figure 7B:
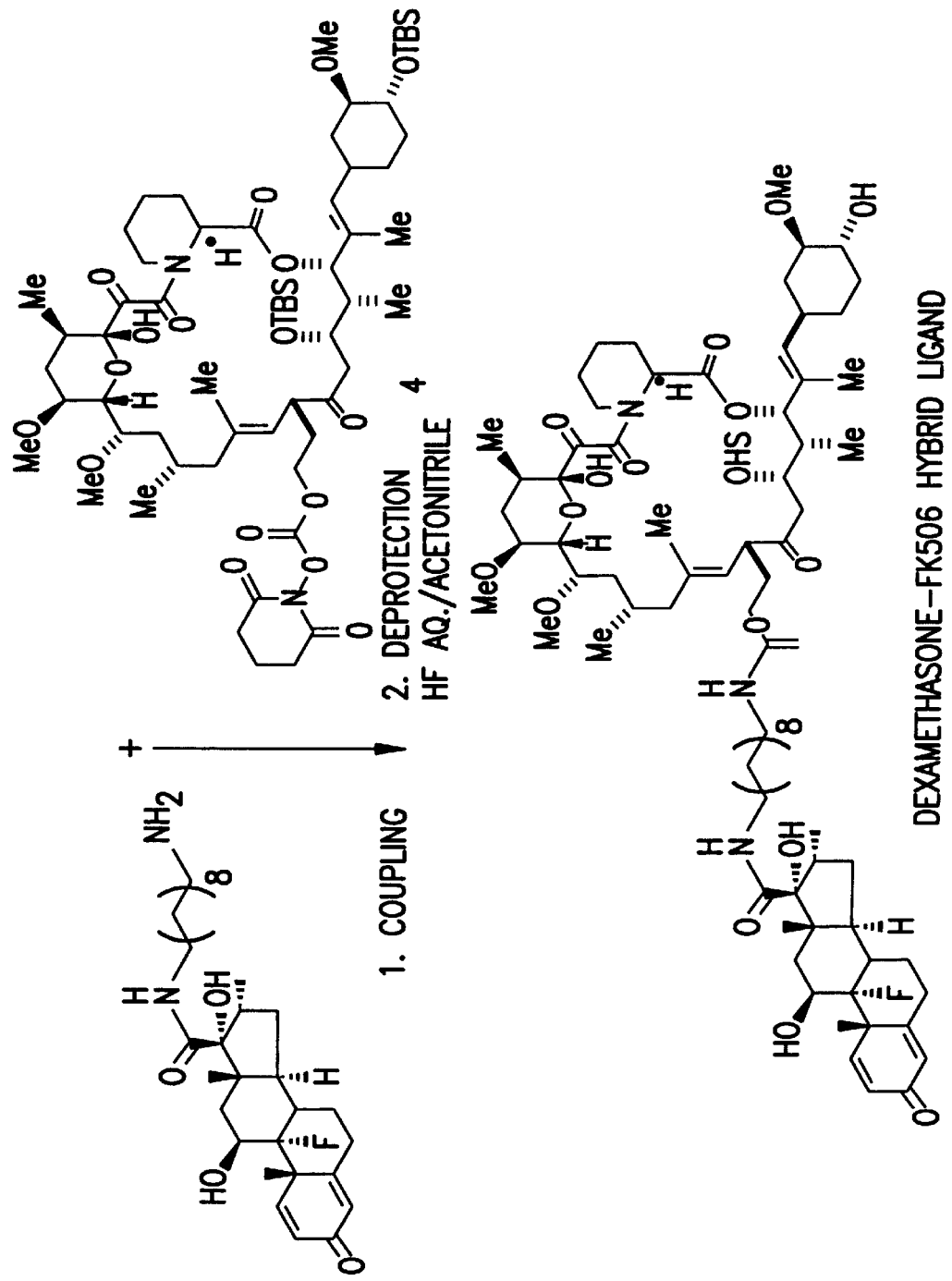

FK506 (Fujisawa Pharmaceuticals) was linked to Dexamethasone (Sigma) to form a hybrid molecule. The chemistry utilized to effect the linkage is shown in FIG. 7. The dexamethasone -FK506 hybrid molecule was synthesized utilizing a convergent synthesis of nine total synthetic transformations with the longest linear sequence being 7 steps. The dexamethasone portion of the hybrid molecule was synthesized as dexamethasone free amine (2) starting from commercially available dexamethasone (1) in three synthetic modifications. The FK506 portion of the hybrid molecule was synthesized as the N-hydroxysuccinamide activated ester (4) from the natural product FK506 (3) in a total of four synthetic modifications. The dexamethasone amine (2) was then coupled to the FK506 activated ester (4) through the formation of an amide bond and several protecting groups were removed to afford the dexamethasone –FK506 hybrid molecule (FIG. 7).

Construction of a Vector Encoding a Hybrid Protein of FKBP-Transcriptional Activator A first vector containing the cDNA fragment encoding FKBP 12-transcriptional module was formed as follows. The cDNA encoding FKBP 12 was originally obtained from a human cDNA library prepared according to well known techniques (Current Protocols in Molecular Biology). The cDNA encoding the FKBP12 was amplified by PCR and subcloned into the EcoRI and XhoI sites of the pJG4-5 vector where the pJG4-5 vector already contains the transcriptional activator module. (Current Protocols in Molecular Biology). The resulting vector is called pJGFKBP.

Construction of the Vector Encoding the Hybrid Protein of Hormone Binding Domain Rat Glucocorticoid Receptor—Lex A DNA Binding Domain.

A second vector encoding the hormone binding domain of rat glucocorticoid receptor (FIG. 4) and the Lex A binding protein was made as follows: A clone containing the full length rat glucocorticoid receptor with the C656G mutation was obtained according to Chakrabati et al. Journal of Biological Chemistry, (1991) vol 266, pp22075–22078. A fragment encoding amino acid residues 497–795 of the protein with the F620S mutation was generated by a standard two-step PCR reaction routinely used for the creation of point mutations. This fragment was flanked by restriction sites for MfeI and XhoI, and was subcloned into the EcoRI and XhoI sites of the pEG202 vector (Current Protocols in Molecular Biology) where the pEG202 vector contains the sequence which encodes for a protein which binds the bacterial Lex A operator. The resulting hybrid construct, designated pEGHDP encodes the second hybrid protein in the assay.

A third vector identified as pSH18-34 and containing the lacZ reporter gene downstream of a number of Lex A operators was made following standard techniques. (Current Protocols in Molecular Biology).

The Yeast Strain

Saccharomyces cerevisiae (EGY 48) [Current Protocols on Molecular Biology], was transformed with the three vectors described above using standard lithium acetate transformation procedures. Positive transformants were selected by plating cells on complete minimal media yeast dropout plates containing 2% glucose, and lacking histidine, tryptophan and uracil. The transformed EGY48 yeast were then screened as described below.

Three Hybrid Screen and Appropriate Controls

Hybrid ligand, Dexamethasone-FK506, was introduced into a population of yeast cells which had previously been transformed with vectors encoding: the Lex A DNA Binding Domain-Hormone Binding Domain of the Rat Glucocorticoid Receptor; lacZ reporter; and transcriptional activator-FKBP12. (FIG. 6). The transformed EGY48 strain was plated onto complete minimal media Ura⁻, His⁻, Trp⁻yeast dropout plates containing 2% galactose, X-Gal, and 1 μM dexamethasone-FK506 hybrid ligand. A light blue color signifying reporter gene activation, began to arise at approximately 36 hours and the yeast were blue at three days. This experiment demonstrated that the trimeric complex could be formed in vivo (FIG. 6). This experiment was also performed on similar plates which were also leu⁻. The leu 2 gene is used in EGY48 as a second reporter gene. Only yeast that grow in the absence of leucine contain a trimeric complex. These yeast grew well, with isolated colonies clearly visible at two days. Two control experiments were conducted by plating the transformed EGY48 strain onto complete minimal media Ura⁻, His⁻, Trp⁻yeast dropout plates as in the aforementioned cases except the plates contained 2% glucose instead of 2% galactose. In the absence of galactose, the hybrid transcriptional activator-FKBP12 protein was not expressed since the gene encoding it is under the Gal1 promoter. Consequently, a trimeric complex could not form and all yeast were either white on X-Gal or did not grow in the absence of leucine. A competitive assay was performed as an additional control . The above yeast strain was plated onto complete minimal media Ura⁻, His⁻, Trp⁻ yeast dropout plates containing 2% galactose, 1 μM dexamethasone-FK506 hybrid ligand and 10 μM FK506. In this experiment all of the yeast remained white. This confirmed that FK506 competitively inhibited the formation of the trimeric complex required for activation of the Lac Z gene, and underscored the specificity of the ligands for the target molecules.

Isolation of cDNA Clones Expressing Protein that Binds Hybrid Ligand

The yeast strain: EGY48 ura3 trp1 his3 Lex A operator-LEU 2; was transformed with pEGHDP and PSH18-34 and plated onto synthetic complete (SC) medium (His⁻, Ura⁻). The resultant EGY48 harboring pEGHBD and pSH18-34 was transformed with a Jurkat cDNA library subcloned into pJG4-5. The transformed yeast cells (1.62×10⁶) were plated onto SC medium (pH6.5, His⁻, Ura⁻, Trp⁻, Leu⁻) containing galactose and 1 μM dexamethasone-FK506. Colonies were collected between days four and ten. All colonies were plated onto SC medium (His⁻, Ura⁻, Trp⁻, Leu⁻) containing galactose. Colonies that displayed growth independent of the presence of hybrid ligand were discarded. The remaining colonies were plated onto SC medium (pH6.5, His⁻, Ura⁻, Trp⁻, Leu⁻) containing galactose and 1 μM dexamethasone-FK506 in the presence of 10 μM FK506. Those colonies whose growth could be completely inhibited by FK506 are grown in liquid culture. The hybrid vectors containing cDNA fused with a transcription activation module were retrieved from these three yeast strains and transformed into E. coli DH5a for preparation of the plasmids. The DNA inserts in these plasmids were sequenced by an ABI automated sequencer and were found to encode human FKBP12.

EXAMPLE 2

Identification of the Cellular Component that Binds to FK506 using a Yeast System Based on Gal4 DNA-Binding Domain and Activation Domain A three-hybrid assay using a second Gal4 DNA binding domain and activation domain as described by Fields et al. (U.S. Pat. No. 5,468,614) and by Durfee et al. (1993) Genes and Development vol 7, pg 555–569 was evaluated. The hormone binding domain of rat glucocorticoid receptor (residues 497–795) containing either a single or double mutations (C656G and F620S) was PCR amplified using primers tagged with restriction sites and subcloned into the vector pASII to encode a fusion protein between the Gal4 DNA binding domain and the hormone binding domain of rat glucocorticoid receptor to give a plasmid pASHBD. The coding sequence of human FKBP12 was PCR amplified and subcloned into the vector pACTII to include a fusion protein between Gal 4 activation domain and human FKBP12. The resultant vector is called pACTFKBP. The vectors pASHBD and pACTFKBP were transformed into the yeast strain Y190 using lithium acetate method and the transformed yeast were selected on SC (Leu⁻, Trp⁻). The transformed yeast strain, Y190/pASHBD-pACTFKBP, were streaked on plates (Leu⁻, Trp⁻, His⁻) containing 30 mM 3-aminotriazole and 1 μM dexamethasone-FK506 in the presence or absence of 10 μM of FK506. In three days, yeast colonies were visible on plates that lack FK506 but are absent from the plate containing 10 μM FK506. These experiments demonstrate that the three-hybrid interaction can be established in the yeast system based on Gal4 DNA-binding domain and activation domain. Furthermore, these experiments show that this yeast system can be used for screening for ligands that compete for an established three-hybrid ligand protein interaction that would possess FKBP binding activities similar to that of FK506.

The above yeast system has both a His- biosynthetic gene and a LacZ reporter gene as reporters for detection of three-hybrid interactions. We performed liquid β-galactosidase assay as follows. A colony of Y190/pASHBD-pACTFKBP was inoculated into liquid SC medium (Leu⁻, Trp⁻, pH6.5) containing 1 μM of dexamethasone-FK506 in the absence or the presence of varying concentrations of FK506. The culture were shaken vigorously at 30° C. for 12–16 hours. The yeast were harvested and the amount of β-galactosidase activity were quantified using established procedure (Current Protocol in Molecular Biology, Chapt. 13). It was shown that there was very low level of β-galactosidase activity in the absence of dexamethasone-FK506. In the presence of increasing concentrations of FK506 (1 to 10 μM), the mount of β-galactosidase activity decrease in a FK506 dose-dependent manner. This system is applied for screening a cDNA library to identify FKBPs that binds to FK506. The screening procedures are identical to those employed in Example 1.

EXAMPLE 3

Establishment of Yeast Three-Hybrid System Using Alternative Ligands

The sensitivity and specificity of the three-hybrid system can be enhanced using a hybrid ligand that forms a covalent bond to a target protein, such as suicide inhibitors of enzymes. In this example, the β-lactam antibiotics and their enzyme targets are used.

Since β-lactamase are used as a selection marker for amplifying most vectors in bacteria, the existing yeast expression vectors are not suitable for use in a three-hybrid system based on β-lactam and their targets. The vectors are modified to replace the β-lactamase selection marker with a kanamycin or chloramphenicol selection marker. This is accomplished by inserting a kanamycin resistance gene into the coding region of β-lactamase gene through the use of a unique restriction site or standard mutagenesis methods. Thus, the vectors described in examples 1 and 2 can be modified to contain kanamycin resistance gene. Subsequently, β-lactamase or penicillin binding protein cDNAs can be subcloned into these vectors to express fusion proteins with either Lex A DNA binding domain or Gal 4 DNA binding domains.

A wide variety of β-lactam antibiotics may be linked covalently with FK506 or dexamethasone. Dimers are tested using the transformed yeast strains appropriate for selected reporter genes as described above (ECY 48 for Lex A and Y190 for Gal 4). These assays have utility for screening for molecular targets of small ligands and for screening for small molecule ligands that bind to predetermined receptor targets.

EXAMPLE 4

Identification of a Small Molecule Capable of Binding to a Selected Target Molecule A population of yeast cells which have previously been transformed with vectors according to Example 1 where the first hybrid protein is hormone-binding domain of the rat glucocorticoid receptor fused to Lex A DNA-binding domain, and the second hybrid protein is FKBP12 fused to a transcriptional activator module and the reporter gene is Lac Z. A 96-well plate is prepared such that each well contains a single member of the hybrid ligand library composed of dexamethasone covalently linked to a library of small molecules. The transformed yeast is grown in each well and a blue coloration is looked for. Those wells expressing the reporter gene are identified and structural information on the corresponding hybrid ligand is retrieved.

EXAMPLE 5

Competitive Assay for Identifying a Small Molecule Ligand Having a Binding Affinity for a Known Target A population of yeast cells which have previously been transformed with vectors according to Example 1 are placed in a 96 well dish. These yeast cells were transformed with DNA encoding a first hybrid protein which is the hormone-binding domain of the rat glucocorticoid receptor fused to Lex A DNA-binding domain, and a second hybrid protein which is FKBP12 fused to a transcriptional activator module and a third vector containing the reporter Lac Z gene. A single member of a ligand library covalently linked to a dexamethasone-FK506 hybrid ligand prepared according to Example 1 was added to each well containing the yeast. Those wells which were identified as having a blue coloring were scored as negative while those wells that appeared white were scored positive. Control wells having either hybrid ligand only or no hybrid molecule were included. The samples are identified according to the absence of expression of the reporter gene; and the ligand from the library is characterized so as to determine its structure information.

EXAMPLE 6

Assay for Identifying a Diagnostic Reagent for Screening for Small Molecule Contaminants in the Environment A cDNA transcriptional activator fusion library is prepared from immune cells (B-cells) capable of producing antibodies to a specific small molecule contaminant, in this case, DDT. Using the screening assay described in Example 1, a hybrid molecule is formed from dexamethasone/DDT by means of an amide linkage as described in FIG. 9. Yeast cells are transformed accordingly with the cDNA fusion library, a vector encoding the hybrid protein containing hormone binding domain of the rat glucocorticoid receptor and a vector encoding the reporter gene Lac Z and the hybrid ligand is introduced so as to identify target molecules. The positive clones are identified by the blue coloration. The vector containing the cDNA from positively staining cells is isolated and the protein product utilized as a reagent in environmental screening assays to detect DDT with high affinity.

EXAMPLE 7

A Three Hybrid Screening Assay Kit

A kit is prepared that contains a plasmid encoding the Lex A DNA binding module fused to the rat glucocorticoid receptor according to Example 1; a plasmid encoding the transcriptional activation domain fused to fragments in a cDNA library; and a reporter plasmid containing Lac Z, GFP or luciferase. The cDNA library for use in the kit is selected from a variety of sources including T-cells, cardiac cells and liver cells, the choice being dependant on the characteristics of the potential target protein and the small molecule. The kit contains a conserved ligand for reacting with a small molecule to form a hybrid molecule by standard coupling procedures described in FIG. 9. Although a number of linkages may be exploited including ester, ether and amide bonds, we have selected an amide bond in this example. In addition, the kit provides an environment, in this case, yeast cells, for permitting the three hybrid screening assay to occur.

We claim:

1. A method for identifying which if any small molecule from a pool of candidate small molecules binds a known first target in a population of cells, comprising:
   (a) with respect to each candidate small molecule, forming a hybrid ligand by chemical linkage of the small molecule to a known molecule, the known molecule binding a known second target;
   (b) introducing each hybrid ligand into the cells, each cell containing;
      (i) a first expression vector, including a DNA encoding the known first target, linked to a coding sequence for a first transcriptional module for expression as a first hybrid protein;
      (ii) a second expression vector including DNA encoding the known second target, linked to a coding sequence for a second transcriptional module for expression as a second hybrid protein; and
      (iii) a third vector including a reporter gene wherein expressing the reporter gene is conditioned on the proximity of the first and second hybrid proteins;
   (c) permitting the hybrid ligand to bind to the first hybrid protein and the second hybrid protein so as to activate the expression of the reporter gene;
   (d) selecting which sample expresses the reporter gene; and
   (e) identifying the small molecule that binds the first target.

2. A method according to claim 1, wherein the cells are genetically altered.

3. A method according to claim 1, wherein the cells are eukaryotic cells.

4. A method according to claim 1, wherein the environment in step (b) is s selected from the group consisting of insect cells, yeast cells, mammalian cell, and their lysates.

5. A method according to claim 3, wherein the cells are yeast cells.

6. A method according to claim 3, wherein the cells are mammalian cells.

7. A method according to claim 5, further comprising the step of enhancing the permeability of the yeast membrane.

8. A method according to claim 7, wherein the step of enhancing the permeability of the yeast membrane further comprises selecting yeast mutants having enhanced membrane permeability.

9. A method according to claim 1, further comprising introducing the hybrid molecule into the cells by electroporation.

10. A method according to claim 1, wherein the first and second transcription module of step (b) (i) and (ii) is selected from the group consisting of a DNA binding protein and a transcriptional activator.

11. A method according to claim 1, wherein the pool of candidate small molecules of step (a) is a pool of candidate steroid molecules.

12. A method according to claim 1, wherein the small molecule is obtained from a combinatorial library.

13. A method according to claim 12, wherein the small molecule is obtained from a combinatorial library of small organic molecules.

14. A method according to claim 1, wherein the small molecule is an environmental contaminant.

15. A method according to claim 1, wherein the reporter gene is selected from the group consisting of Lac Z, GFP, luciferase and an antibody coding region.

16. A method according to claim 14, wherein the steps (b)–(e) of the method are iteratively repeated, in the presence of a preparation of random small molecules for competitive binding with the hybrid ligand so as to identify an additional small molecule capable of competitively binding the first target.

17. A method for identifying a protein target to which a small molecule is capable of binding, comprising:
- (a) providing a hybrid ligand consisting essentially of a first small molecule ligand, identified as ligand A and a second molecule identified as ligand B, that are covalently linked by chemical synthesis, wherein ligand A has a specificity for a first preselected protein target and ligand B has a specificity for a second unknown protein target;
- (b) introducing the hybrid ligand into a population of cells, each cell containing;
  - (i) a first expression vector, including DNA encoding the first protein target for ligand A, linked to a coding sequence for a first transcriptional module for expression as a first hybrid protein;
  - (ii) a second expression vector including a random DNA fragment encoding the second protein target linked to a second transcriptional module for expression as a second hybrid protein; and
  - (iii) a third vector including a reporter gene wherein the expression of the reporter gene is conditioned on the proximity of the first and second hybrid proteins;
- (c) permitting the hybrid ligand to bind the first hybrid protein through ligand A and the second hybrid protein through ligand B so as to activate the expression of the reporter gene;
- (d) selecting the cells expressing the reporter gene; and
- (e) identifying the second protein target in the samples selected in (d).

18. A kit for detecting interactions between pharmacologically relevant small molecules and proteins, comprising;
- (a) a preactivated small molecule ligand A and reagents for forming a hybrid molecule with at least one type of small molecule ligand B;
- (b) a first expression vector including DNA encoding the binding protein for Ligand A linked to a coding sequence for a first transcriptional module for expression as a first hybrid protein;
- (c) a second expression vector including a random DNA fragment encoding a polypeptide linked to a coding sequence for a second transcriptional module for expression as a second hybrid protein;
- (d) a third vector including a reporter gene wherein transcription of the reporter gene is conditioned on the proximity of the first and second hybrid proteins;
- (e) an environment for transcription and translation of the hybrid proteins and the reporter gene; and
- (f) a signal to detect the expression of the reporter gene following the formation of a trimeric complex between the hybrid ligand and the hybrid proteins.

19. A method according to claim 17, wherein the second expression vector of step (b) (ii) contains a random DNA fragment of a size suited for encoding a gene product, wherein the DNA fragment is from a library of DNA.

20. A method according to claim 19, wherein the DNA fragments in the library are selected from the group consisting of genomicDNA, cDNA and syntheticDNA.

21. A method according to claim 17, wherein the DNA fragment of step (b) (ii) is obtained from a plurality of libraries.

22. A method according to claim 20, wherein the cDNA library is derived from an immune cell.

23. A method according to claim 20, wherein the cDNA is derived from an immune cell capable of producing an immune response to the ligand B.

24. A method according to claim 17, wherein ligand B has a known biological function.

25. A method according to claim 17, wherein the population of cells are genetically altered.

26. A method according to claim 25, wherein the cells are eukaryotic cells.

27. A method according to claim 26, wherein the population of cells is selected from the group consisting of insect cells, yeast cells and mammalian cell.

28. A method according to claim 27, wherein the cells are yeast cells.

29. A method according to claim 27, wherein the cells are mammalian cells.

30. A method according to claim 28, further comprising the step of enhancing the permeability of the yeast membrane.

31. A method according to claim 30, wherein the step of enhancing the permeability of the yeast membrane further comprises selecting yeast mutants having enhanced membrane permeability.

32. A method according to claim 17, wherein step (b) further comprises introducing the hybrid ligand into the cells by electroporation.

33. A method according to claim 17, wherein the steps (b)–(e) of the method are repeated iteratively in the presence of a preparation of random small molecules for competitive binding with the hybrid ligand and identifying the small molecule capable of competitively binding the second hybrid protein.

* * * * *